United States Patent [19]

Mura et al.

[11] Patent Number: 4,797,357

[45] Date of Patent: Jan. 10, 1989

[54] LIGHT-STABLE REDUCIBLE COMPOUNDS AND ANALYTICAL COMPOSITIONS, ELEMENTS AND METHODS UTILIZING SAME

[75] Inventors: Albert J. Mura; Paul B. Merkel, both of Rochester, N.Y.

[73] Assignee: Eastman Kodak Company, Rochester, N.Y.

[21] Appl. No.: 868,479

[22] Filed: May 30, 1986

[51] Int. Cl.$^4$ .......................... C12Q 1/04; C07C 50/00

[52] U.S. Cl. ........................................ 435/34; 436/169; 436/172; 436/80 C; 436/805; 436/807; 436/904; 260/396 R

[58] Field of Search ............... 436/169, 172, 800, 805, 436/807, 904; 558/412, 417; 560/27, 28, 115, 110; 435/34; 260/396 R

[56] References Cited

U.S. PATENT DOCUMENTS

| | | | |
|---|---|---|---|
| 3,980,479 | 9/1976 | Fields et al. | 430/222 |
| 4,108,850 | 8/1978 | Fields et al. | 534/650 |
| 4,139,379 | 2/1979 | Chasman et al. | 430/223 |
| 4,144,306 | 3/1979 | Figueras | 422/56 |
| 4,232,107 | 11/1980 | Janssens | 430/223 |
| 4,307,188 | 12/1981 | White | 435/4 |
| 4,371,604 | 2/1933 | Van de Sande et al. | 430/223 |
| 4,746,607 | 5/1988 | Mura | 435/25 |

OTHER PUBLICATIONS

Hackh's Chemical Dictionary 4th Edition, 1969, McGraw-Hill Book Co., New York, p. 499.

Davies et al., "A Dictionary of Electrochemistry" pp. 189–194, John Wiley & Sons, NY 1976.

Lingane "Electroanalytical Chemistry" 2nd Edition, Interscience Pulishers Inc., NY, 1958, pp. 260–264.

Van de Sande, Angew. Chem. Int. Ed. Engl., 22 pp. 191–209 (1983).

Primary Examiner—Robert J. Warden
Assistant Examiner—Robert Benson
Attorney, Agent, or Firm—J. Lanny Tucker

[57] ABSTRACT

Certain reducible aromatic and quinone compounds having bulky groups on the carbamate nitrogen atom have improved stability to light. These compounds are useful in analytical compositions, elements and methods, e.g. for assays of bacterial cells. These compounds have suitable substituents that promote the release of phenalenone or benzphenalenone fluorescent dyes at physiological pH.

18 Claims, No Drawings

LIGHT-STABLE REDUCIBLE COMPOUNDS AND ANALYTICAL COMPOSITIONS, ELEMENTS AND METHODS UTILIZING SAME

FIELD OF THE INVENTION

This invention relates to clinical chemistry. In particular, it relates to the use of certain reducible compounds in dry or wet assays of liquids, such as biological liquids, to detect living cells (e.g. bacteria) or other analytes. It also relates to novel reducible compounds.

BACKGROUND OF THE INVENTION

Chemical analysis of liquids, such as water, milk and biological fluids is often desirable or necessary for health maintenance and diagnostic care. Various compositions and elements to facilitate such analyses are known. Such compositions and elements generally include a reagent composition for determining a chemical or biological substance under analysis, identified as an analyte herein. The reagent composition, upon interaction with the analyte, provides a detectable change (e.g. dye formation).

Recently, much work has been directed to developing compositions and elements which are useful for rapid and highly quantitative diagnostic or clinical analysis of biological fluids such as whole blood, serum, plasma, urine and the like.

For example, for the rapid and effective diagnosis and treatment of infectious diseases, it is desirable to be able to detect the bacteria causing the disease as rapidly as possible. Infections of the urinary tract are among the most common bacterial diseases, second in frequency only to infections of the respiratory tract. In fact, in many hospitals, urinary tract infections are the most common form of nosocomial infections, often following the use of in-dwelling catheters and various surgical procedures. Most urinary tract infections (UTI) result from ascending infection by microorganisms introduced through the urethra and vary in severity from an unsuspected infection to a condition of severe systemic disease. Such infections are usually associated with bacterial counts of 100,000 ($10^5$) or more organisms per ml of urine, a condition referred to as significant bacteriuria. Under normal conditions, urine is sterile, although contamination from the external genitalia may contribute up to 1,000 ($10^3$) organisms per ml in properly collected and transported specimens.

Further, in order to insure that a prescribed antibiotic is in fact effective in treating an infection, repeated tests during therapy are required. The need for simple, rapid bacteriuria testing is thus clear. Moreover, in view of the frequent unsuspected asymptomatic occurrences of UTI among children, pregnant women, diabetics and geriatric populations, diagnosis of which may require collection and testing of several specimens, bacteriuria tests must be sufficiently simple and economical to permit routine performance. Again, this illustrates the need for rapid and inexpensive bacteriuria detection methods.

A significant advance in the art for determination of various analytes, including microorganisms is described in copending and commonly assigned U.S. Ser. No. 824,766, filed Jan. 31, 1986 by Belly et al and entitled REDUCIBLE COMPOUNDS AND ANALYTICAL COMPOSITIONS, ELEMENTS AND METHODS UTILIZING SAME. The reducible compounds therein can be readily reduced in the presence of a reductant to release a detectable species, e.g. a dye, within a matter of minutes. Further, copending and commonly assigned U.S. Ser. No. 824,756, filed Jan. 31, 1986 by Babb et al and entitled BIOLOGICAL AND ANALYTICAL USES OF PHENALENONE AND BENZPHENALENONE COMPOUNDS relates to similar reducible compounds which rapidly release fluorescent phenalenone and benzphenalenone compounds in the presence of reductants. It has been observed, however, when low concentrations of analytes are to be detected that high background is present with some of these reducible compounds. This high background is due to premature reduction caused by the absorption of light.

There is a need for reducible compounds like those described above which readily release fluorescent dyes for the detection of low concentrations of analytes but which have exceptional stability to light.

SUMMARY OF THE INVENTION

The present invention provides reducible compounds having improved light stability which have the structure CAR—$(R^1)_n$ wherein n is 1 or 2, CAR— is a substituted or unsubstituted aromatic or quinone nucleus, and $R^1$ is

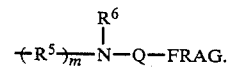

$R^5$ is substituted or unsubstituted alkylene of 1 or 2 carbon atoms, $R^6$ is a substituted or unsubstituted organic group having a molecular weight of at least 40, or together with $R^5$ forms a divalent substituted or unsubstituted heterocyclic group having at least 5 atoms in the ring, Q is carbonyl or thiocarbonyl, FRAG is a species derived from a phenalenone or benzphenalenone dye, m is 0 or 1, provided that when $R^1$ is replaced by H, CAR—H has an $E_{\frac{1}{2}}$ of at least about $+100$ mV when measured in water.

In a preferred embodiment, CAR— is

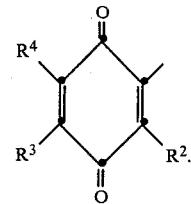

$R^2$ and $R^4$ are independently hydrogen, substituted or unsubstituted alkyl, substituted or unsubstituted aryl or an electron withdrawing group, $R^3$ is $R^1$, substituted or unsubstituted alkyl, substituted or unsubstituted aryl or an electron withdrawing group, provided at least one of $R^2$, $R^3$ and $R^4$ is an electron withdrawing group, or $R^3$ and $R^4$, taken together, represent the atoms necessary to complete a substituted or unsubstituted strained fused carbocyclic ring.

The reducible compound of this invention can be used in an aqueous composition buffered to a pH of 9 or less. Alternatively, it can be included in an analytical element comprising an absorbent carrier material.

Further a method for the determination of an analyte comprises the steps of:

A. at a pH of 9 or less, contacting a sample of a liquid suspected of containing an analyte with the reducible compound described above, and B. determining the phenalenone or benzphenalenone dye released as a result of the presence of the analyte.

The present invention provides a class of novel compounds particularly useful in determinations of chemical or biological compounds. These compounds are readily reduced in the presence of such analytes to give a detectable fluorescent dye. However, these compounds are stable when exposed to light for at least an hour, i.e. there is substantially no premature reduction and release of fluorescent dye. These advantages are achieved by attaching a bulky substituent at the $R^6$ carbamate position of the reducible compound.

DETAILED DESCRIPTION OF THE INVENTION

The reducible compounds of this invention are RIND compounds, i.e. reducible compounds capable of undergoing intramolecular nucleophilic displacement at physiological pH to release one or more fluorescent dyes when a nucleophilic group is generated by at least a one electron reduction of the compound. In other words, such displacement occurs when the RIND compound is reduced by a suitable reductant which provides the necessary electron(s) (described in more detail below).

The term "intramolecular nucleophilic displacement" refers to a reaction in which a nucleophilic center on a molecule reacts at another site in the molecule, which site is an electrophilic center, to effect displacement of a group or atom attached to the electrophilic center. Generally, the RIND compounds useful in this invention have the nucleophilic and electorphilic groups juxtaposed in the threedimensional configuration of the molecule in close proximity whereby the intramolecular reaction can take place and a ring is formed having from 4 to 7 atoms, and preferably having 5 or 6 atoms.

The rate of nucleophilic displacement is substantially zero prior to reduction of the RIND compound. Hence, the RIND compounds are stable prior to that reduction and particularly stable to light.

Preferred RIND compounds are those which have the structure CAR-$R^1$ wherein CAR— is

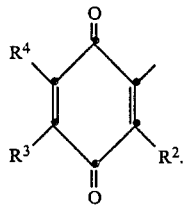

$R^1$ is

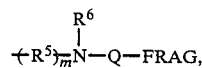

wherein m is 0 or 1, and preferably 1. $R^5$ is substituted or unsubstituted alkylene, preferably of 1 or 2 carbon atoms in the backbone (e.g. methylene, ethylene, alkoxymethylene, etc.). Most preferably, $R^5$ is methylene. Q is carbonyl or thiocarbonyl and preferably carbonyl.

$R^6$ is a substituted or unsubstituted organic group having a molecular weight of at least 40. More particularly, $R^6$ can be substituted or unsubstituted alkyl having at least 3 carbon atoms. The alkyl group preferably has from 3 to 40 carbon atoms, and optionally has alkylene, arylene or cycloalkylene chains interrupted with sulfur, oxygen or other heteroatoms (e.g. n-propyl, isopropyl, t-butyl, hexyl, decyl, lauryl, trifluoromethyl, benzyl, n-propyl-n-butylether, etc.). $R^6$ can also be substituted or unsubstituted aryl preferably of 6 to 40 carbon atoms (e.g. phenyl, xylyl, naphthyl, p-nitrophenyl, anthryl, p-t-butoxyphenyl, p-t-butylcarboxyphenyl, etc.), substituted or unsubstituted cycloalkyl preferably of 4 to 40 carbon atoms (e.g. cyclobutyl, cyclohexyl, 4-methylcyclohexyl, etc.) or substituted or unsubstituted heterocycle preferably of 5 to 40 carbon and hetero atoms (e.g., pyridyl, furanyl, indolyl, quinolinyl, etc.). $R^6$ together with $R^5$, can also form a divalent substituted or unsubstituted cyclic group having at least 5 atoms in the ring, thereby forming a divalent heterocyclic moiety between CAR— and the FRAG moiety of $R^1$ in the structure shown above. Preferably, $R^6$ is substituted or unsubstituted alkyl or substituted or unsubstituted aryl as defined above. Most preferably, $R^6$ is p-t-butylcarboxyphenyl.

FRAG is a species derived from a phenalenone or benzphenalenone fluorescent dye. Preferably, FRAG is derived from a phenalenone dye. Such dyes are described in more detail in U.S. Ser. No. 824,756 of Babb et al, noted above. Particularly useful dyes include

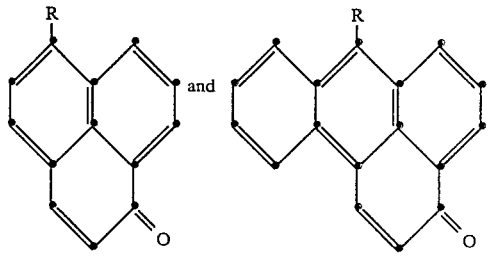

wherein R is hydroxy or mercapto.

FRAG is linked to Q by means of a single bond through a bivalent monoatom linkage which is a part of FRAG. Preferably, the monoatom linkage is oxy or thio, and most preferably it is oxy.

$R^2$, $R^3$ and $R^4$ in the above quinone structure are independently hydrogen, substituted or unsubstituted alkyl of 1 to 40 carbon atoms (e.g. methyl, ethyl, hydroxymethyl, methoxymethyl, benzyl, etc.) sustituted or unsubstituted aryl (e.g. phenyl, naphthyl, methylnaphthyl, p-nitrophenyl, m-methoxyphenyl, etc.) or an electron withdrawing group wwhich generally has a positive Hammett sigma value, and preferably has a sigma value greater than about 0.06. Hammett sigma values are calculated in accordance with standard procedures described, e.g. in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (e.g. fluoro, bromo, chloro, iodo), trihalomethyl (e.g. trifluoromethyl, trichloromethyl, etc.), trialkylammonium, carbonyl, carbamoyl, sulfonyl, sulfamoyl, esters and others known in the art, or alkyl or aryl groups (defined above) substituted with one or more of these electron withdrawing groups. Preferred electron withdrawing groups include p-nitrophenyl, m-nitrophenyl, p-cyanophenyl and 2,5-dichlorophenyl. Aryl groups with methoxy or acetamido groups in the meta position are also useful.

$R^3$ can also be the same as $R^1$, thereby potentially providing 2:1 molar ratio of fluorescent dye molecules to original RIND compound molecules.

Alternatively, $R^3$ and $R^4$, taken together, can represent the carbon atoms necessary to complete a substituted or unsubstituted strained fused carbocyclic ring attached to the quinone nucleus. Ring strain makes reduction potentials more positive (e.g. Rieke et al, *Tetrahedron Letters*, 50, pp. 4381-4384, 1969). For example, such a ring (mono- or bicyclic) can have from 4 to 8 carbon atoms in the backbone. Preferably, the ring is a 5-membered mono-ring, or a 7- or 8-membered bicyclic ring.

The RIND compounds of this invention readily release FRAG at physiological pH (i.e. 9 or less) because of their appropriate $E_{\frac{1}{2}}$ values. The desired $E_{\frac{1}{2}}$ value of the compound is achieved by putting appropriate electron withdrawing groups on the CAR— nucleus, or by a combination of a strained fused ring attached to the nucleus and electron withdrawing groups. $E_{\frac{1}{2}}$ measurements are made according to standard electrochemical techniques using either polarography or cyclic voltametry (see, e.g. Sawyer and Roberts, Jr., *Experimental Electrochemistry for Chemists*, John Wiley & Sons, New York, 1974). Preferably, the $E_{\frac{1}{2}}$ is from about +100 mV to about +400 mV as measured in water. Details of measuring the $E_{\frac{1}{2}}$ are described below.

Representative novel and preferred RIND compounds of this invention are listed in Table I below in reference to the following structure and without intending to limit this invention:

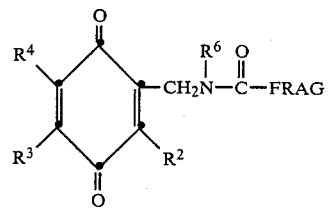

The $E_{\frac{1}{2}}$ values in Table I were determined for the quinone nucleus of this structure having a hydrogen atom in place of

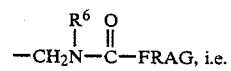

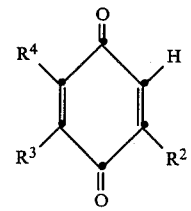

The $E_{\frac{1}{2}}$ values were measured in an aqueous environment, i.e. in an aqueous solution of N,N-dimethylformamide, a nonionic surfactant (TRITON X-100) and sodium phosphate buffer (pH 7). A normal hydrogen electrode was used as a standard.

TABLE I

| RIND Compound | $R^6$ | $R^2$ | $R^3$ $R^4$ | FRAG | $E_{\frac{1}{2}}$ (mV) |
|---|---|---|---|---|---|
| I | —CH₂CH₂CH₂—⟨phenyl⟩ | ⟨phenyl⟩—CN | $R^3$ and $R^4$ together form (5-membered ring) | —O—⟨naphthoquinone⟩ | +220 |
| II | —CH₂CH₂—⟨phenyl⟩ | ⟨phenyl⟩—CN | $R^3$ and $R^4$ together form (5-membered ring) | —O—⟨naphthoquinone⟩ | +220 |
| III | ⟨phenyl⟩—CO₂—t-butyl | ⟨phenyl⟩—CN | $R^3$ and $R^4$ together form (5-membered ring) | —O—⟨naphthoquinone⟩ | +220 |

TABLE I-continued

| RIND Compound | R⁶ | R² | R³  R⁴ | FRAG | $E_{\frac{1}{2}}$ (mV) |
|---|---|---|---|---|---|
| IV | [thiophene ring] | [phenyl-CN] | R³ and R⁴ together form [cyclopropyl-like fused] | —O—[anthraquinone] | +220 |
| V | —CH(CH₃)₂ | [phenyl-CN] | R³ and R⁴ together form | —O—[anthraquinone] | +220 |
| VI | —n-C₁₂H₂₅ | [phenyl-CN] | R³ and R⁴ together form | —O—[anthraquinone] | +220 |

RIND compound III is preferred in the practice of this invention.

The novel RIND compounds of this invention are prepared using a sequence of reactions. Generally, the preparation sequence includes the following general steps: (1) preparation of the substituted hydroquinone, (2) oxazine ring formation, (3) oxazine ring opening, (4) preparation of the carbamoyl chloride, and (5) reaction of a compound from which the FRAG moiety is derived with the carbamoyl chloride. The precursor to the FRAG moiety has a hydroxy or mercapto group which reacts with the carbamoyl chloride. A representative preparation is provided in the Example 1 below.

Other RIND compounds useful in the practice of this invention include those having the appropriate $E_{\frac{1}{2}}$ values and the structure CAR—(R¹)ₙ wherein:

(1) CAR— is a substituted or unsubstituted nucleus of a 1,2-naphthoquinone, 1,2-, 1,4- or 9,10-anthraquinone, 4,4'-diphenoquinone, azuloquinone or 1,6-[10]-anulenoquinone wherein R¹ is attached to the nucleus one carbon atom distant or in the peri position from one of the oxo groups of the nucleus. The nucleus can be substituted with one or more electron withdrawing groups as described above for R² or have one or more strained fused rings as described above for R³ and R⁴.

R¹ is

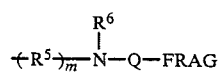

as defined above, and n is an integer of 1 or 2.

(2) CAR— is

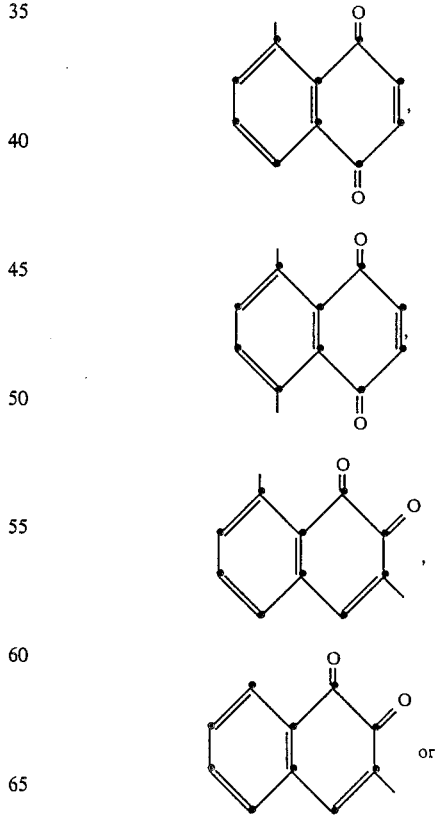

-continued

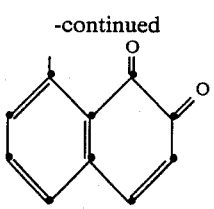

any of which can be substituted with one or more electron withdrawing groups as described above for $R^2$, $R^3$ and $R^4$. $R^1$ is

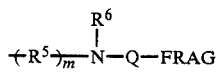

as defined above, and n is 1 or 2.

All of these reducible compounds can be prepared using techniques and starting materials known in the art or readily apparent to a skilled synthetic chemist.

Some of the reducible compounds described herein have limited water solubility. Hence, it is best, when using them in an aqueous environment, to prepare a dispersion of the compound prior to use, e.g. in a coating formulation. Such dispersions generally comprise the reducible compound, an aqueous buffer solution and either a solubilizing surfactant or a water-miscible organic solvent for the compound, or both. The materials useful in such dispersions and the details of their preparation are described in the Belly et al patent application noted above.

Other RIND compounds are water-compatible. Such reducible compounds are described in more detail in copending and commonly assigned U.S. Ser. No. 868,855, filed on even date herewith by Mura et al and entitled WATER-COMPATIBLE REDUCIBLE COMPOUNDS AND THEIR USE IN ANALYTICAL COMPOSITIONS AND METHODS.

The reducible compounds of this invention can be used in an aqueous composition which is effectively buffered to maintain a physiological pH (9 or less). Representative buffers include phosphates, borates and others reported by Good et al in *Biochemistry*, 5, 467 (1966), and *Anal. Biochem.*, 104, 300 (1980).

The reducible compounds described herein are useful in compositions for analytical determination (i.e. qualitative or quantitative detection) of aqueous and nonaqueous liquids, e.g. biological fluids, manufacturing processes, wastewater, food stuffs, etc. Determinations can be made of various analytes, including cells (e.g. bacteria, yeast, fungi, white blood cells etc.), enzymes (e.g. oxidoreductases, such as lactate dehydrogenase, pyruvate dehydrogenase, glucose-6-phosphate dehydrogenase, etc., oxidases, such as glucose oxidase, lactate oxidase, α-glycerophosphate oxidase, etc., transferases, such as alanine aminotransferase, aspartate aminotransferase, etc., hydrolases, such as lipase, carboxyesterase, etc.), biological or chemical reductants other than living cells which will reduce the reducible compound (e.g. ascorbates, cysteine, glutathione, thioredoxin, etc.), metabolizable substances (e.g. glucose, lactic acid, triglycerides, cholesterol, etc.), immunoreactants (e.g. antigens, antibodies, hpatens, etc.), and other determinations made via a single reaction or sequence of reactions which brings about reduction of the compound and release of a fluorescent dye.

The compositions can be used to monitor enzyme redox reactions as well as flavin adenine dinucleotide (FAD-FADH)-based and nicotinamide adenine dinucleotide (NAD-NADH)-based and (NADP-NADPH)-based reactions. In such instances, the reducible compound can be used to provide a fluorescent dye in place of NADH.

The reducible compounds of this invention, are particularly useful in detecting or quantifying living cells in biological samples. Although any biological sample suspected of having living cells therein (e.g. food, tissue, ground water, cooling water, pharmaceutical products, sewage, etc.) can be analyzed for bacteria, yeast, fungi, etc. by this invention, the invention is particularly useful for microbial detection in aqueous liquids, such as human and animal fluids (e.g. urine, cerebral spinal fluid, blood and the like as well as stool secretions) and suspensions of human or animal tissue. The practice of this invention is particularly important for detection of urinary tract infections in urine (diluted or undiluted).

When determining living cells using the reducible compounds, it is preferable for rapid dye release in such determinations that the living cells interact with an electron transfer agent (herein ETA). The presence of an ETA may also provide more efficient dye release for analytical determinations of nonliving analytes. The ETA is a mobile compound which acts as an intermediary between the substance being determined (e.g. living cell) and the reducible compound.

In general, the ETA compounds useful in the practice of this invention have an $E_{\frac{1}{2}}$ in the range of from about $-320$ to about $+400$ mV as measured in aqueous buffer (pH 7) versus the normal hydrogen electrode using a differential pulse polarographic technique with a PAR Potentiostat (Princeton Applied Research, Princeton, N.J. In general, the potential of the ETA should be more positive than the potential of the substance to be determined (i.e. analyte) and less positive than the potential of the RIND compound. That is, the ETA should be more easily reduced than the analyte and less easily reduced than the reducible compound. They are generally present at a concentration that is dependant upon the concentration of the analyte, and preferably at a concentration of from about $1 \times 10^{-3}$ molar to about $1 \times 10^{-7}$ molar.

ETA compounds useful in the practice of this invention include phenazine methosulfate, phenazine ethosulfate and similar compounds known to one skilled in the art. Combinations of different ETA compounds can be used if desired. Preferred ETA compounds useful in the practice of this invention which provide further advantages of low background are those describe in copending and commonly assigned U.S. Ser. No. 699,374 of Mura et al filed Feb. 7, 1985. In general, those compounds are substituted benzo- and naphthoquinones. Examples of this class of quinones include 2,3-dimethyl-5-hydroxymethyl-1,4-benzoquinone, 2,5-dimethoxy-1,4-benzoquinone, 2,3,5-trimethyl-1,4-benzoquinone, 2,6-dimethoxy-1,4-benzoquinone, 2-hydroxymethyl-1,4-naphthoquinone and 2-(2-hydroxyethyl)-1,4-naphthoquinone.

The detection of living cells, and particularly of bacterial cells, is often carried out in the presence of a nutrient for those cells although its presence is not essential. Any nutrient medium can be used which contains useful carbon, and optionally nitrogen, sources. Suitable nutrient media having proper components and pH are well known in the art.

The present invention is adaptable to either solution or dry assays. In a solution assay, a solution (or dispersion) containing a reducible compound, and preferably an ETA, is prepared and contacted (i.e. mixed) with a liquid test sample suspected of containing the living cells or analyte to be determined. The ETA can also be mixed with the test sample prior to mixing with the reducible compound. Generally the reducible compound is mixed with the test sample in a suitable container (e.g. test tube, petri dish beaker, cuvette, etc.). The resulting solution (or dispersion) is gently mixed and incubated for a relatively short time (i.e. up to about 30 minutes) at a temperature up to about 40° C., and generally from about 20 to about 40° C. The test sample is then evaluated by measuring the fluorescence of the released dye. Such an evaluation can be done with suitable fluorometric equipment.

A solution assay can also be carried out by contacting a porous, absorbent material, e.g. paper strip, containing the test sample with a composition containing the reducible compound. The analyte in the test sample can migrate from the porous material into the dispersion and initiate the analytical reactions needed for determination. In solution assays, the amount of reducible compound present is at least about 0.001, and preferably from about 0.01 to about 1.0, millimolar. Other reagents can be present in amounts readily determined by one skilled in the art.

Alternatively, the method of this invention can be practiced in a dry assay with a dry analytical element. Such an element can be composed of a absorbent carrier material, i.e. a thin sheet or strip of self-supporting absorbent or bibulous material, such as filter paper or strips, which contains the reducible compound or a dried residue of the dispersion comprising same. Such elements are known in the art as test strips, diagnostic elements, dip sticks, diagnostic agents and the like.

When employed in dry analytical elements, the reducible compounds described herein can be incorporated into a suitable absorbent carrier material by imbibition or impregnation, or can be coated on a suitable absorbent carrier material. Alternatively, they can be added to the element during an assay. Useful carrier materials are insoluble and maintain their structural integrity when exposed to water or physiological fluids such as urine or serum. Useful carrier materials can be prepared from paper, porous particulate structures, cellulose, porous polymeric films, glass fibers, woven and nonwoven fabrics (synthetic and nonsynthetic) and the like. Useful materials and procedures for making such elements are well known in the art as exemplified by U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al) and 4,270,920 (issued June 2, 1981 to Kondo et al).

A dry assay can be practiced to particular advantage with an analytical element comprising a nonporous support having thereon at least one porous spreading zone as the absorbent carrier material. The reducible compound can be in the spreading zone or in a different zone (e.g. reagent zone, registration zone, hydrophilic zone, etc.).

The spreading zone can be prepared from any suitable fibrous or non-fibrous material or mixtures of either or both, either mixed with a suitable binder material or woven into a fabric, as described in U.S. Pat. Nos. 4,292,272 (issued Sept. 29, 1981 to Kitajima et al), 3,992,158 (issued Nov. 16, 1976 to Przbylowicz et al), 4,258,001 (issued Mar. 24, 1981 to Pierce et al) and 4,430,436 (issued Feb. 7, 1984 to Koyama et al) and Japanese Pat. Publication Nos. 57(1982)-101760 (published June 24, 1982). It is desired that the spreading zones be isotropically porous, meaning that the porosity is the same in each direction in the zone as created by interconnected spaces or pores between particles, fibers, polymeric strands, etc.

The nonporous support can be any suitable dimensionally stable, and preferably, transparent (i.e. radiation transmissive) film or sheet material which transmits electromagnetic radiation of a wavelength between about 200 and about 900 nm. Useful support materials include polystyrene, polyesters [e.g. poly(ethylene terephthalate)], polycarbonates, cellulose esters (e.g. cellulose acetate), etc.

The elements can have more than one zone, e.g. a reagent zone, a registration zone, subbing zone, etc. The zones are generally in fluid contact with each other, meaning that fluids, reagents and reaction products can pass between superposed regions of adjacent zones. Preferably, the zones are separately coated superposed layers, although two or more zones can be a single coated layer.

In the elements of this invention, the amount of the reducible compound can be varied widely, but it is generally present in a coverage of at least about 0.01, and preferably from about 0.05 to about 0.2, $g/m^2$. Optional, but preferred reagents (e.g. ETA, nutrient, buffer, etc.) are generally present in the following coverages:

ETA: generally at least about 0.001, and preferably from about 0.01 to about 1, $g/m^2$, nutrient: generally at least about 0.05, and preferably from about 0.1 to about 2, $g/m^2$ (used only in living cell detection), and buffer (pH$\leqq$9): generally at least about 0.1, and preferably from about 0.5 to about 2, $g/m^2$.

One or more of the zones can contain a variety of other desirable, but optional, components, including activators, binders (generally hydrophilic), antioxidants, coupler solvents, etc. as is known in the art, as well as any reagents needed for assay of a particular analyte.

In one embodiment of this invention, an element for detection of living organisms (e.g. yeast, fungi, bacteria, etc.) in an aqueous liquid comprises an electron transfer agent and a reducible compound, both of which are described above. It is desirable that these elements also contain a nutrient for the living cells and a buffer which maintains physiological lpH during the assay (e.g. when contacted with a 1–200 $\mu l$ sample of test liquid). Such an element can be used to detect bacteria, for example, in a urine sample (e.g. one pretreated to eliminate interferents or to concentrate cells) by physically contacting the sample and element in a suitable manner so that sample and reagents in the element are mixed, and detecting the dye released from the reducible compound as a result of the presence of the bacteria at the appropriate wavelength.

In another embodiment of this invention, an element is used for the determination of a nonliving biological or chemical analyte in an aqueous liquid. If the analyte is not capable of directly reducing the reducible compound described herein to release dye, the assay also includes the use of an interactive composition comprising one or more reagents which interact with the analyte to produce a product which will reduce the reducible compound. This interactive composition can be incorporated into the element or added at the time of the assay. Examples of such analytes are described above. The amount of dye detected can be correlated to the amount of analyte present in the liquid sample.

A variety of different elements, depending on the method of assay, can be prepared in accordance with the present invention. Elements can be configured in a variety of forms, including elongatged tapes of any desired width, sheets, slides or chips.

The assay of this invention can be manual or automated. In general, in using the dry elements, an analyte or living cell determination is made by taking the element from a supply roll, chip packet or other source and contacting it with a sample (e.g. 1–200 $\mu$l) of the liquid to be tested so that the sample mixes with the reagents in the element. Such contact can be accomplished in any suitable manner, e.g. dipping or immersing the element into the sample or, preferably, by spotting the element by hand or machine with one or more drops of the sample with a suitable dispensing means.

After sample application, the element can be exposed to conditioning, such as incubation, heating or the like, that may be desirable to quicken or otherwise facilitate obtaining any test result.

Detection of an analyte or living cell is achieved when the reducible compound is reduced releasing a phenalenone or benzphenalenone dye which can be detected using standard fluorometric apparatus and detection procedures.

Reagents used in the following examples were obtained as follows: brain heart infusion (BHI) broth and YM broth medium from Difco Labs (Detroit, Mich., U.S.A.), TRITON X-100 surfactant from Rohm & Haas (Philadelphia, Pa., U.S.A.), and the microorganisms from the American Type Culture Collection (ATCC) in Rockville, Md., U.S.A. All other reagents were either obtained from Eastman Kodak Company (Rochester, N.Y., U.S.A.) or prepared using known starting materials and procedures.

*Escherichia coli* (*E. coli*), ATCC 25922, and *Staphylococcus aureus* (*S. aureus*), ATCC 25923, were grown overnight in BHI medium at 37° C. without shaking and transferred daily. Forty milliliters of the cells that were grown overnight were harvested by centrifugation, washed and resuspended in 0.05 molar HEPES buffer (pH 7.8). HEPES is N-2-hydroxyethylpiperazine-N'-2-ethanesulfonic acid. The absorbance measured at 620 nm was adjusted to 0.83 and 1.0 respectively. An absorbance of 0.1 (620 nm) has been found to be equivalent to about $6 \times 10^7$ cells/ml. *Candida albicans* (*C. albicans*), ATCC 14053, was grown in YM broth medium at 25° C. with shaking and transferred daily. The cells were harvested and washed as described above. The absorbance at 620 nm was adjusted to 1.0.

In the preparation of the illustrated reducible compounds, the identity and purity of the intermediates were determined by infrared (IR) spectra as measured with a commercially available Perkin-Elmer 137 spectrophotometer [sharp(s) or broad(b) bands yielding structural information are reported in reciprocal centimeters (cm$^{-1}$)], by nuclear magnetic resonance (NMR) spectra measured with a standard Perkin-Elmer EM 390 NMR spectrophotometer [chemical shifts reported in $\delta$ values in ppm to tetramethylsilane at broad(b), singlet(s), multiplet(m) or broad singlets(bs) peaks], or by field desorption mass spectral analysis (FDMS) measured with a Varian MAT 731 spectrophotometer. The identity and purity of final products were determined by IR, NMR spectroscopy, FDMS analysis and elemental analysis.

The following examples are presented to illustrate the practice of this invention. The identified RIND compounds are the reducible compounds included in Table I above.

EXAMPLE 1

Preparation of RIND Compound

RIND compound III of Table I was prepared in the following manner.

The quinone nucleus was prepared by a standard oxidation of the corresponding hydroquinone, which had been prepared according to the procedure described in Steps 1–3 of Example 1 in U.S. Ser. No. 824,766 of Belly et al, referenced above, using p-cyanoaniline instead of p-nitroaniline.

This quinone (5.2 g, 18 mmole) was added to a mixture of hydrobromic acid (30% in acetic acid, 48 ml), 37% formalin (18 ml) and acetic acid (140 ml), and the resulting solution was heated at 55° C. for 18 hours. After cooling, the reaction mixture was poured into ice water (500 ml), and the precipitated yellow solid was collected and recrystallized from ethanol to give 2.4 g of the bromomethyl intermediate having a m.p. of 201–202° C. An NMR spectrum confirmed the structure.

A mixture of the bromomethyl intermediate (9.2 g, 24 mmole), p-amino-t-butylbenzoate (9.25 g, 48 mmole) and silver(I)carbonate (6.6 g, 24 mmole) in N,N-dimethylformamide (360 ml) was stirred under a nitrogen atmosphere in a dark area for 36 hours. The resulting mixture was poured into dilute hydrochloric acid/ice water (1500 ml) and the precipitated brown solid was collected by filtration, washed with water and dried under reduced pressure in a desiccator. Chromatography (silica, 70:30 ligroine:ethyl acetate) afforded the desired amine intermediate, yield of 7 g. Mass spectral analyses, nuclear magnetic resonance and infrared spectroscopy confirmed the structure.

The amine intermediate was converted to the corresponding carbamoyl chloride by the procedure described in Step 6, Example 1 of the Belly et al application noted above.

A mixture of the carbamoyl chloride (7 g, 12.6 mmole), 6-hydroxyphenalenone (2.05 g, 10.4 mmole), prepared by the procedure described in U.S. Ser. No. 824,756 of Babb et al, noted above, and N,N-dimethylaminopyridine (catalytic amount) in pyridine (75 ml) was stirred under nitrogen in a dark area for 18 hours. The mixture was poured into dilute hydrochloric acid/ice water and the precipitated solid was collected by filtration, washed with water and dried in air in a dark area. Chromatography (silica, 98:2, dichloromethane:acetone) afforded 5 g of the desired product, RIND III. An analytical sample was obtained by recrystallization from ether to give a pale yellow solid. NMR (CDCl$_3$)$\sigma$, 1.2–2.0 (m, —CH$_2$CH$_2$— of bicyclic ring), 1.6 (s,t-butyl), 3.21–3.59 (m, bridgehead H's), 4.9 (s, —CH$_2$N—), 6.6–6.75 (d, dye H's), 7.1–8.2 (m, dye and aryl H's), 8.6–8.7 (d, dye H's). IR (KBr) cm$^{-1}$, 2240 (s, CN), 1720 (b, C=O), 1640 (s, quinone).

EXAMPLE 2

Light Stability of RIND Compounds

This is a comparative example showing the improved light stability of several RIND compounds of this invention over a RIND compound outside the scope of this invention.

The RIND compound outside the scope of this invention used as the Control is described in the Belly et al application U.S. Ser. No. 824,766 noted above, and has the following structure:

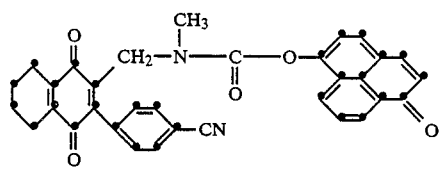

This compound has a methyl group as $R^6$, which group has a molecular weight less than 40.

All of the RIND dispersions were prepared as follows: the RIND compound (5 mg) was dissolved in N,N-dimethylformamide (0.5 ml), TRITON X-100 (1.0 ml) was added and the solution was stirred. A portion (0.5 ml) of this solution was then added to potassium phosphate buffer (25 ml, pH 7.5, ionic strength 0.75).

A sample of each dispersion was irradiated with light from either a mercury or xenon arc lamp which had been passed through a 33-86-02 monochromator available from Bausch and Lomb (Rochester, N.Y., U.S.A.). Light intensity impinging upon the samples was measured with a standard radiometer, and fluorescent dye release was monitored by measuring the change in absorption spectra at 425 or 437 nm using a standard spectrophotometer. Table II below shows the amount of dye released (fluorescent yield) for each RIND compound in terms of number of molecules reduced per photon of light absorbed. The RIND compounds of the present invention (from Table I above) released significantly less dye in response to light than the Control RIND compound.

TABLE II

| RIND Compound | Fluorescent Yield |
| --- | --- |
| Control | 0.031 (425 nm) |
| " | 0.034 (437 nm) |
| I | 0.01 (425 nm) |
| III | 0.0016 (437 nm) |
| IV | 0.01 (437 nm) |
| V | 0.015 (437 nm) |

EXAMPLE 3-5

Determination of Bacteria and Yeast in Dry Elements

These examples illustrate the determination of two species of bacteria, E.coli and S.aureus and of a yeast, C.albicans, using dry elements containing RIND III of Table I above.

Strips of Whatman 3 mm chromatography paper (VWR Scientific, Rochester, N.Y., U.S.A.) were immersed in the following solution: 7 ml methanol, 1 ml RIND solution (RIND III, 0.028 molar in N,N-dimethylformamide containing 0.1% sulfuric acid), 1 ml ETA solution (2,3-dimethoxy-5-methyl-1,4-benzoquinone, 0.01 molar in methanol) and 1 ml glucose solution (10% solution in water). The strips were then allowed to dry at 25° C. for 1 hour in a dark area.

A standard paper punch was used to cut discs (about 0.6 cm in diameter) from the dried strips and the discs were placed in Corning Cell Wells TM. (Corning Glass Works, Corning, N.Y., U.S.A.).

Ten microliter samples of Controls (containing only buffer) and test cell suspensions E.coli, about $5 \times 10^8$ cells/ml, S.aureus, about $5 \times 10^8$ cells/ml, and C.albicans, about $5 \times 10^6$ cells/ml) were spotted onto the paper discs and fluorescence (excitation at 540 nm, emission at 620 nm) was measured at 0 minutes and after 30 minutes at 37° C. using a Dynatech Microfluor Reader (Dynatech Labs, Alexandria, Va., U.S.A.). The results are shown in Table III below as the change in fluorescence after 30 minutes. The average of two readings is listed. The present invention was demonstrated to be useful in determining living organisms.

TABLE III

| | Δ Relative Fluorescence, 30 Minutes |
| --- | --- |
| Control | 25 |
| E. coli | 505 |
| S. aureus | 475 |
| C. albicans | 471 |

The present invention has been described in detail with particular reference to preferred embodiments thereof, but it will be understood that variations and modifications can be effected within the spirit and scope of the invention.

We claim:

1. A reducible compound of the structure CA-R—(R$^1$)$_n$ wherein n is 1 or 2, CAR— is a substituted or unsubstituted aromatic or quinone nucleus selected from the group consisting of

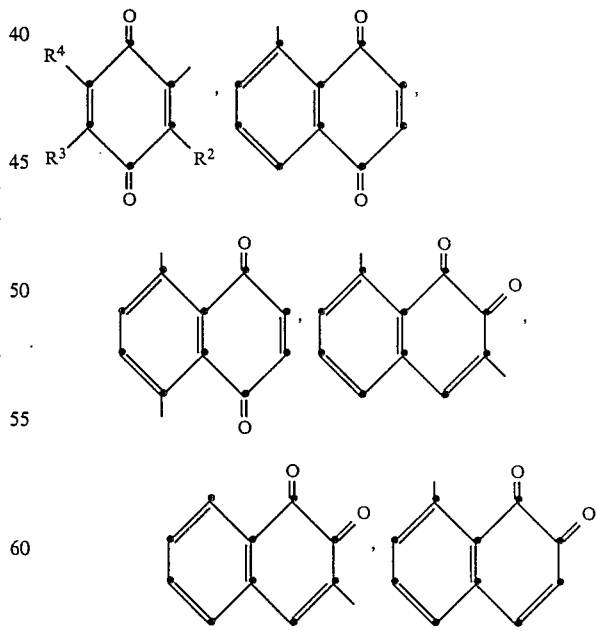

and the nucleus of a 1,2-, 1,4- or 9,10-anthraquinone, 4,4'-diphenoquinone, azuloquinone, or 1,6-anulenoquinone wherein $R^1$ is attached to the nucleus adjacent to one of the oxo groups of the nucleus, and $R^1$ is

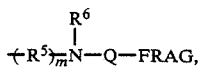

R² and R⁴ are independently hydrogen, substituted or unsubstituted alkyl, substituted or unsubstituted aryl or an electron withdrawing group, R³ is the same as R¹, hydrogen, substituted or unsubstituted alkyl, substituted or unsubstituted aryl or an electron withdrawing group, provided that at least one of R², R³ and R⁴ is an electron withdrawing group, or R³ and R⁴, taken together, represent the atoms necessary to complete a substituted or unsubstituted strained fused carbocyclic ring, R⁵ is substituted or unsubstituted alkylene of 1 or 2 carbon atoms, R⁶ is a substituted or unsubstituted organic group having a molecular weight of at least 40, or together with R⁵ forms a divalent substituted or unsubstituted heterocyclic group having at least 5 atoms in the ring, Q is carbonyl or thiocarbonyl, FRAG is a moiety derived from a phenalenone or benzphenalenone dye selected from the group consisting of

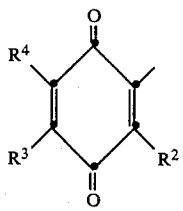

wherein R is hydroxy or mercapto, and
m is 0 or 1, provided that when R¹ is replaced with H, CAR-H has an $E_{\frac{1}{2}}$ of at least about +100 mV when measured in water using a normal hydrogen electrode as a standard.

2. The compound of claim 1 wherein CAR— is

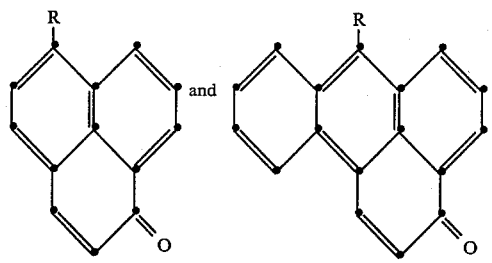

3. The compound of claim 2 wherein m is 1, and R³ and R⁴, taken together, represent the atoms necessary to complete a substituted or unsubstituted strained fused 4- to 7-membered carbocyclic ring.

4. The compound of claim 1 wherein R⁶ is substituted or unsubstituted alkyl having at least 3 carbon atoms, substituted or unsubstituted aryl, substituted or unsubstituted cycloalkyl, substituted or unsubstituted heterocycle, or together with R⁵ forms a divalent substituted or unsubstituted heterocyclic group having at least 5 atoms.

5. The compound of claim 4 wherein R⁶ is substituted or unsubstituted alkyl having at least 3 carbon atoms or substituted or unsubstituted aryl.

6. A composition buffered at a pH of 9 or less and comprising a reducible compound of the structure CAR$-$(R¹)$_n$ wherein n is 1 or 2, CAR— is a substituted or unsubstituted aromatic or quinone nucleus selected from the group consisting of

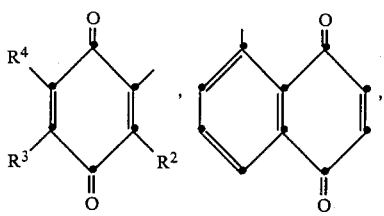

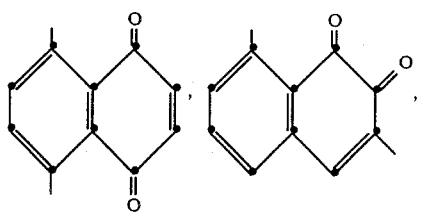

and the nucleus of a 1,2-, 1,4- or 9,10-anthraquinone, 4,4'-diphenoquinone, azuloquinone, or 1,6-anulenoquinone wherein R¹ is attached to the nucleus adjacent to one of the oxo groups of the nucleus, and
R¹ is

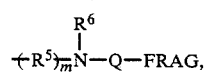

R² and R⁴ are independently hydrogen, substituted or unsubstituted alkyl, substituted or unsubstituted aryl or an electron withdrawing group, R³ is the same as R¹, hydrogen, substituted or unsubstituted alkyl, substituted or unsubstituted aryl or an electron withdrawing group, provided that at least one of R², R³ and R⁴ is an electron withdrawing group, or R³ and R⁴, taken together, represent the atoms necessary to complete a substituted or unsubstituted strained fused carbocyclic ring, R⁵ is substituted or unsubstituted alkylene of 1 or 2 carbon atoms, R⁶ is a substituted or unsubstituted organic group having a molecular weight of at least 40, or together with R⁵ forms a divalent substituted or unsubstituted heterocyclic group having at least 5 atoms in the ring, Q is carbonyl or thiocarbonyl, FRAG is a moiety derived from a phenalenone or benzphenalenone dye selected from the group consisting of

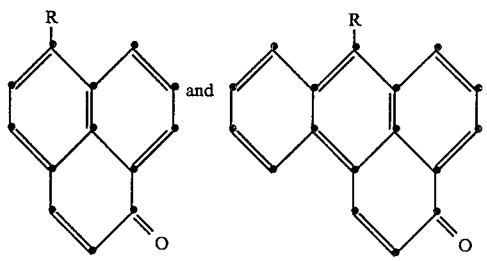

wherein R is hydroxy or mercapto, and
m is 0 or 1,
provided that when $R^1$ is replaced with H, CAR—H has an $E_{\frac{1}{2}}$ of at least about +100 mV when measured in water using a normal hydrogen electrode as a standard.

7. The composition of claim 6 wherein CAR— is

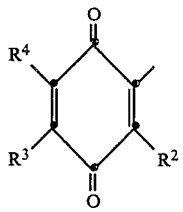

8. The composition of claim 6 wherein $R^6$ is substituted or unsubstituted alkyl having at least 3 carbon atoms, substituted or unsubstituted aryl, substituted or unsubstituted cycloalkyl, substituted or unsubstituted heterocycle, or together with $R^5$ forms a divalent substituted or unsubstituted heterocyclic group having at least 5 atoms.

9. A dry analytical element for the determination of an analyte comprising an absorbent carrier material and containing a reducible compound of the structure CAR—$R^1)_n$ wherein n is 1 or 2, CAR— is substituted or unsubstituted aromatic or quinone nucleus selected from the group consisting of

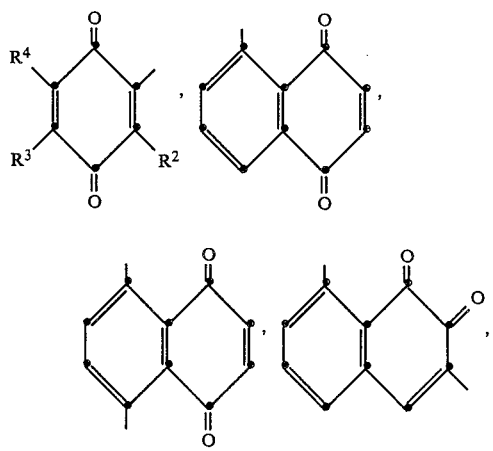

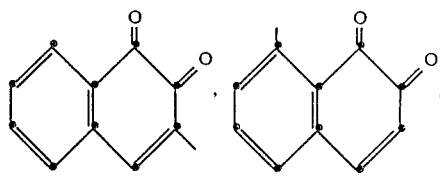

and the nucleus of a 1,2-, 1,4- or 9,10-anthraquinone, 4,4'-diphenoquinone, azuloquinone, or 1,6-anulenoquinone wherein $R^1$ is attached to the nucleus adjacent to one of the oxo groups of the nucleus, and
$R^1$ is

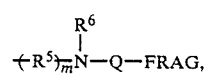

$R^2$ and $R^4$ are independently hydrogen, substituted or unsubstituted alkyl, substituted or unsubstituted aryl or an electron withdrawing group, $R^3$ is the same as $R^1$, hydrogen, substituted or unsubstituted alkyl, substituted or unsubstituted aryl or an electron withdrawing group, provided that at least one of $R^2$, $R^3$ and $R^4$ is an electron withdrawing group, or $R^3$ and $R^4$, taken together, represent the atoms necessary to complete a substituted or unsubstituted strained fused carbocyclic ring, $R^5$ is substituted or unsubstituted alkylene of 1 or 2 carbon atoms, $R^6$ is a substituted or unsubstituted organic group having a molecular weight of at least 40, or together with $R^5$ forms a divalent substituted or unsubstituted heterocyclic group having at least 5 atoms in the ring, p1 Q is carbonyl or thiocarbonyl, FRAG is a moiety derived from a phenalenone or benzphenalenone dye selected from the group consisting of

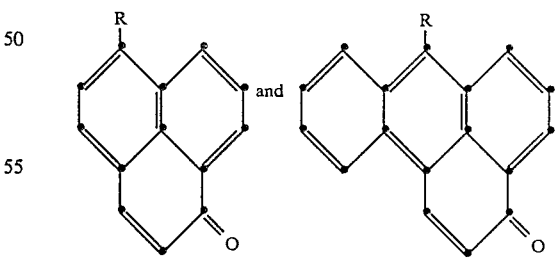

wherein R is hydroxy or mercapto, and
m is 0 or 1,
provided that when $R^1$ is replaced with H, CAR—H has an $E_{\frac{1}{2}}$ of at least about +100 mV when measured in water using a normal hydrogen electrode as a standard.

10. The element of claim 9 wherein CAR— is

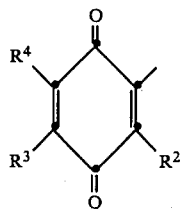

11. The element of claim 9 further comprising an ineractive composition for an analyte, said composition comprising one or more reagents which interact with said analyte to produce a product which will reduce said reducible compound.

12. The element of claim 9 further comprising a support carrying said absorbent carrier material.

13. The element of claim 9 further comprising a living cell nutrient.

14. A method for the determination of an analyte comprising the steps of:
 A. at a pH of 9 or less, contacting a sample of a liquid suspected of containing an analyte with a reducible compound of the structure CAR$-(R^1)_n$ wherein n is 1 or 2, CAR— is a substituted or unsubstituted aromatic or quinone nucleus selected from the group consisting of

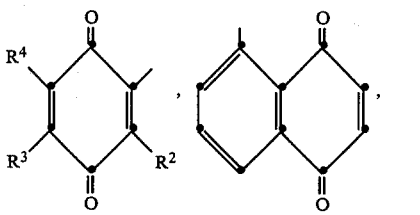

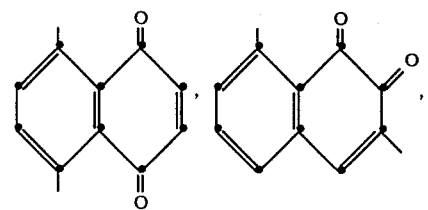

and the nucleus of a 1,2-, 1,4- or 9,10-anthraquinone, 4,4'-diphenoquinone, azuloquinone, or 1,6-anulenoquinone wherein $R^1$ is attached to the nucleus adjacent to one of the oxo groups of the nucleus, and $R^1$ is

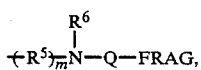

$R^2$ and $R^4$ are independently hydrogen, substituted or unsubstituted alkyl, substituted or unsubstituted aryl or an electron withdrawing group, $R^3$ is the same as $R^1$, hydrogen, substituted or unsubstituted alkyl, substituted or unsubstituted aryl or an electron withdrawing group, provided that at least one of $R^2$, $R^3$ and $R^4$ is an electron withdrawing group, or $R^3$ and $R^4$, taken together, represent the atoms necessary to complete a substituted or unsubstituted strained fused carbocyclic ring, $R^5$ is substituted or unsubstituted alkylene of 1 or 2 carbon atoms, $R^6$ is a substituted or unsubstituted organic group having a molecular weight of at least 40, or together with $R^5$ forms a divalent substituted or unsubstituted heterocyclic group having at least 5 atoms in the ring, Q is carbonyl or thiocarbonyl, FRAG is a moiety derived from a phenalenone or benzphenalenone dye selected from the group consisting of

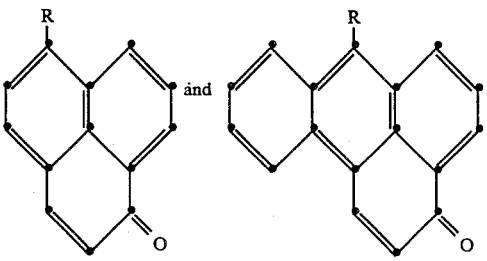

wherein R is hydroxy or mercapto, and
m is 0 or 1,
provided that when $R^1$ is replaced with H, CAR—H has an $E_{\frac{1}{2}}$ of at least about +100 mV when measured in water using a normal hydrogen electrode as a standard, and B. determining the phenalenone or benzphenalenone dye released as a result of the presence of said analyte.

15. The method of claim 14 wherein CAR— is

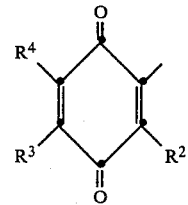

16. The method of claim 14 for the determination of a nonliving analyte in the presence of an interactive composition for said analyte, said composition comprising one or more reagents which interact with said analyte to produce a product which will reduce said reducible compound.

17. The method of claim 14 for the determination of living cells in the presence of an electron transfer agent and nutrient for said cells.

18. The method of claim 17 for the determination of microorganisms in a urine sample.

* * * * *

UNITED STATES PATENT AND TRADEMARK OFFICE
CERTIFICATE OF CORRECTION

PATENT NO. : 4,797,357
DATED : January 10, 1989
INVENTOR(S) : Albert J. Mura and Paul B. Merkel It is certified that error appears in the above-identified patent and that said Letters Patent is hereby corrected as shown below Bridging Columns 5 and 6 of Compounds I, II, III and Bridging Columns 7 and 8 of Compounds IV, V and VI, the part of the formula reading " 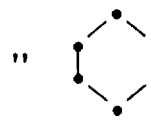 " should read --  --;

Column 15, lines 13-20, the part of the formula reading

" 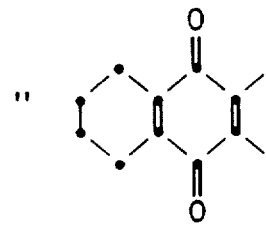 " should read -- 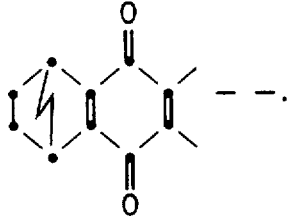 --.

Signed and Sealed this

Fifteenth Day of May, 1990

*Attest:*

HARRY F. MANBECK, JR.

*Attesting Officer*     *Commissioner of Patents and Trademarks*